United States Patent
Wen et al.

(10) Patent No.: US 11,011,365 B2
(45) Date of Patent: May 18, 2021

(54) MASS SPECTROMETRY SYSTEM AND WORKING METHOD AND APPLICATION THEREOF, AND SAMPLING DEVICE USED THEREIN

(71) Applicants: NINGBO UNIVERSITY, Zhejiang (CN); CHINA INNOVATION INSTRUMENT CO., LTD., Zhejiang (CN)

(72) Inventors: Luhong Wen, Zhejiang (CN); Peng Zhao, Zhejiang (CN); Ruiqiang Chen, Zhejiang (CN); Huanhuan Hong, Zhejiang (CN); Feng Zhou, Zhejiang (CN)

(73) Assignees: NINGBO UNIVERSITY, Ningbo (CN); CHINA INNOVATION INSTRUMENT CO., LTD, Ningbo (CN)

( * ) Notice: Subject to any disclaimer, the term of this patent is extended or adjusted under 35 U.S.C. 154(b) by 0 days.

(21) Appl. No.: 16/286,574

(22) Filed: Feb. 26, 2019

(65) Prior Publication Data
US 2019/0198309 A1 Jun. 27, 2019

Related U.S. Application Data

(63) Continuation of application No. PCT/CN2017/114955, filed on Dec. 7, 2017.

(30) Foreign Application Priority Data

Dec. 31, 2016 (CN) .......................... 201611268645.9

(51) Int. Cl.
*H01J 49/04* (2006.01)
*H01J 49/42* (2006.01)
(Continued)

(52) U.S. Cl.
CPC ............ *H01J 49/426* (2013.01); *G01N 27/64* (2013.01); *G01N 33/543* (2013.01);
(Continued)

(58) Field of Classification Search
None
See application file for complete search history.

(56) References Cited

U.S. PATENT DOCUMENTS

| 6,508,986 B1 * | 1/2003 | Anderson | ................. B01L 9/54 |
| | | | 250/288 |
| 2003/0057368 A1 * | 3/2003 | Franzen | .............. H01J 49/0418 |
| | | | 250/281 |

(Continued)

FOREIGN PATENT DOCUMENTS

| CN | 102637574 A | 8/2012 |
| CN | 103443898 A | 12/2013 |

(Continued)

OTHER PUBLICATIONS

Colletes et al. "A new insert sample approach to paper spray mass spectrometry: a paper substrate with paraffin barriers" Analyst 141, 1707-1713 (2016) (Year: 2016).*

(Continued)

*Primary Examiner* — James Choi

(57) ABSTRACT

A mass spectrometry system and a working method and an application thereof, and a sampling device. The mass spectrometry system includes an ion source, a sampling device and a mass spectrometer. The sampling device includes: a guide rail; a support adapted to move on the guide rail; a bearing member made from a hydrophobic material with two ends being fixed to the support; a plurality of containers for containing samples arranged on the support; a plurality of transport members made from a hydrophilic material and including a first portion provided on the bearing member and a second portion connected to the first portion and extending (Continued)

into each container; adjacent transport members being not in contact; and a drive module configured to drive the support to move on the guide rail such that a central axis of an exit port of the ion source passes through the first portion.

11 Claims, 4 Drawing Sheets

(51) Int. Cl.
G01N 27/64 (2006.01)
H01J 49/06 (2006.01)
G01N 33/543 (2006.01)

(52) U.S. Cl.
CPC ...... H01J 49/0413 (2013.01); H01J 49/0431 (2013.01); H01J 49/062 (2013.01); *H01J 49/0409* (2013.01)

(56) References Cited

U.S. PATENT DOCUMENTS

| | | | | |
|---|---|---|---|---|
| 2004/0021071 A1* | 2/2004 | Mordekhay | ......... | H01J 49/0413 250/288 |
| 2005/0045815 A1* | 3/2005 | Bui | ............ | H01J 49/0004 250/282 |
| 2010/0044563 A1* | 2/2010 | Harada | ............ | H01J 49/164 250/288 |
| 2012/0119079 A1* | 5/2012 | Ouyang | ............ | H01J 49/0431 250/282 |
| 2016/0018361 A1 | 1/2016 | Trimpin et al. | | |
| 2016/0099138 A1* | 4/2016 | Hoehndorf | ......... | H01J 49/0418 250/453.11 |
| 2018/0012746 A1* | 1/2018 | Ouyang | ............ | H01J 49/0409 |

FOREIGN PATENT DOCUMENTS

| | | | |
|---|---|---|---|
| CN | 103797559 A | | 5/2014 |
| CN | 204528320 U | * | 8/2015 |
| CN | 204951607 U | | 1/2016 |
| CN | 106960777 A | | 7/2017 |
| CN | 206441693 U | | 8/2017 |
| WO | 2016130646 A1 | | 8/2016 |

OTHER PUBLICATIONS

Huang "Infrared laser ablation for biological mass spectrometry" PhD thesis, Louisiana State University and Agricultural and Mechanical College (2012) (Year: 2012).*

Peng et al. "Reactive-Electrospray-Assisted Laser Desorption/Ionization for Characterization of Peptides and Proteins" Anal. Chem. 80, 6995-7003 (2008) (Year: 2008).*

* cited by examiner

MASS SPECTROMETRY SYSTEM AND WORKING METHOD AND APPLICATION THEREOF, AND SAMPLING DEVICE USED THEREIN

CROSS-REFERENCE TO RELATED APPLICATIONS

This application is a continuation of International Patent Application No. PCT/CN2017/114955, filed on Dec. 7, 2017, which claims the benefit of priority from Chinese Application No. 201611268645.9, filed on Dec. 31, 2016. The contents of the aforementioned applications, including any intervening amendments thereto, are incorporated herein by reference.

TECHNICAL FIELD

The present invention relates to mass spectrometry, and in particular to a mass spectrometry system and a working method and an application thereof, and a sampling device for mass spectrometry.

BACKGROUND OF THE INVENTION

An open-type ion source for mass spectrometer is a new ion source which is used in an open atmospheric environment. Such ion source enables in-situ, real-time and fast ionization of samples within a very short time without complicated sample pretreatment. In addition, this ion source also has the advantages of small size and portability, low cost and wide range of application, etc. Therefore, it can be widely used in various fields such as food detection, pharmaceutical analysis, environment monitoring, public safety and clinical diagnosis.

Currently, when liquid samples are analyzed by a mass spectrometer with an open-type ion source (DBDI, LTP, etc.), the samples are generally introduced with a capillary tube or a glass rod. In this way, however, there is a relatively high background noise, and it is difficult to analyze bio-macromolecular samples such as polypeptides, proteins, since a large number of high-energy particles are present in the ejected plasma. Paper-based sampling can eliminate some high-energy particles in plasma to weaken ionization energy, reducing the background noise and thus improving the analytical sensitivity.

However, this method has many disadvantages.

1. Manual sampling only introduces human factors, and automatic and high-throughput analysis of samples is not available.

2. During the test, the paper-based hydrophilic region (a dropping region) remains wet, which is good for the ionization of samples, allowing for higher analytical sensitivity. However, liquid sample drops added in the paper-based hydrophilic region is usually 3-10 µL which is too volatile to keep each hydrophilic region wet during array analysis. That is, it is difficult to ensure the analytical sensitivity and reproducibility and to perform a high-throughput analysis.

SUMMARY OF THE INVENTION

To solve the deficiencies in the prior art, the present invention provides a mass spectrometry system with automatic sampling and high sensitivity and reproducibility.

A mass spectrometry system comprises an ion source, a sampling device and a mass spectrometer; wherein the sampling device includes:

a guide rail;
a support adapted to move on the guide rail;
a bearing member made from a hydrophobic material; wherein two ends of the bearing member are fixed to the support;
a plurality of containers for containing samples arranged on the support;
a plurality of transport members made from a hydrophilic material; wherein each of the transport members comprises a first portion provided on the bearing member and a second portion connected to the first portion and extending into each of the plurality of containers; and adjacent transport members are not in contact;
a drive module configured to drive the support to move on the guide rail such that a central axis of an exit port of the ion source passes through the first portion.

Another object of the present invention is to provide a method for operating the mass spectrometry system, comprising:

(A1) delivering a sample in the container by capillarity to the first portion corresponding to the sample;
(A2) driving the support to move on the guide rail such that plasma is ejected from the ion source to the first portion to ionize the sample; and
(A3) analyzing ions by the mass spectrometer; and proceeding to step (A2) to measure individual samples separately.

The present invention provides the following benefits compared to the prior art.

1. Movement of the first portion on the support is automatically and accurately controlled by the drive module such that the samples on respective first portions are ionized separately. Accordingly, interference caused by human factors is eliminated to improve the accuracy of analysis. The automatic and high-throughput analysis of samples is thus realized.

2. The first portion can be kept wet for a long time during the analysis of samples (on the first portions in an array arrangement), facilitating the ionization of samples, so as to ensure the sensitivity and reproducibility of the analysis.

3. The system is simple and easy to operate, so that the detection efficiency can be improved.

BRIEF DESCRIPTION OF THE DRAWINGS

The disclosure of the present invention will become more apparent with reference to the drawings. It should be understood by those skilled in the art that these drawings are merely illustrative of the present invention, and are not intended to limit the scope of the present invention. In the drawings.

DETAILED DESCRIPTION OF EMBODIMENTS

FIGS. 1-4 and the following description describe optional embodiments of the present invention to teach those skilled in the art how to implement and reproduce the present invention. To teach the technical solutions of the present invention, some conventional aspects have been simplified or omitted. It should be understood by those skilled in the art that variants or substitutions derived from these embodiments shall fall within the scope of the present invention. It should also be understood by those skilled in the art that the following features can be combined in various ways to form a plurality of variants of the present invention. Therefore, the present invention is not limited to the following optional embodiments, but only defined by the appended claims and equivalents thereof.

EXAMPLE 1

Figure 1:
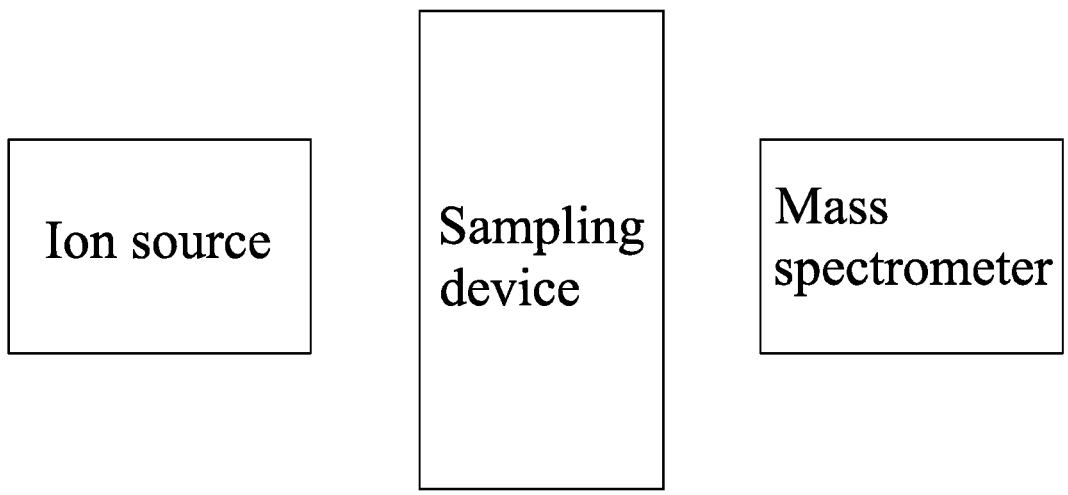
FIG. 1 is a schematic diagram of a mass spectrometry system according to an embodiment of the present invention.

FIG. 1 schematically shows a mass spectrometry system according to an embodiment of the present invention. As shown in FIG. 1, the mass spectrometry system includes an ion source and a mass spectrometer, which are arranged on two sides of a sampling device, respectively.

Figure 2:
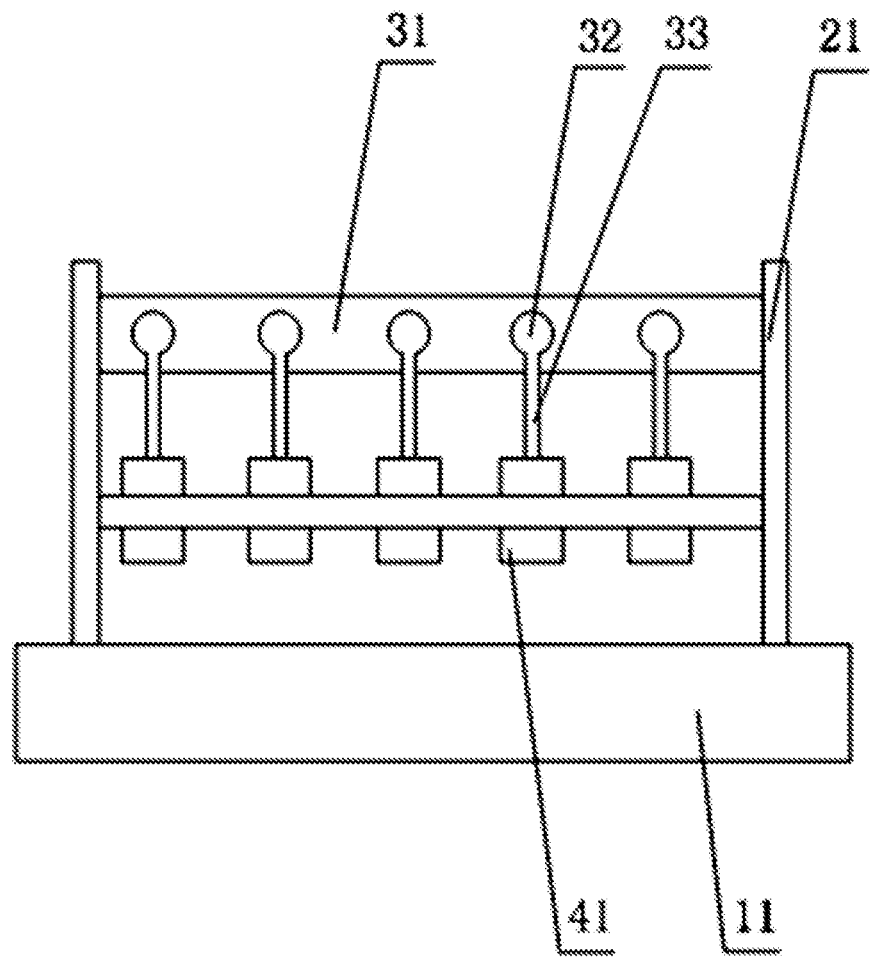
FIG. 2 is a schematic diagram of a sampling device according to an embodiment of the present invention.

FIG. 2 schematically shows a sampling device according to an embodiment of the present invention. As shown in FIG. 2, the sampling device includes:

a guide rail 11 arranged horizontally;

a support 21 adapted to move on the guide rail 11;

a bearing member 31 made from a hydrophobic material which is arranged horizontally with two ends fixed to the support;

a plurality of containers 41 for containing samples which are arranged on the support;

a plurality of transport members made from a hydrophilic material; where each of the transport members comprises a first portion 32 arranged on the bearing member and a second portion 33 connected to the first portion and extending into the container 41; adjacent transport members are not in contact; each of the transport members is arranged vertically, and the transport members are arranged on the bearing member from left to right; and a through hole is provided on the bearing member at a position where the first portion is provided; and a drive module (not shown, for example, a step motor) configured to drive the support to move on the guide rail such that a central axis of an exit port of the ion source passes through the first portion.

The present embodiment also provides a method for operating the mass spectrometry system comprising the following steps:

(A1) delivering various samples in the containers by capillarity to respective first portions corresponding to the various samples;

(A2) driving the support to move on the guide rail such that plasma is ejected from the ion source to the first portions to ionize the samples; and (A3) analyzing ions by a mass spectrometer; and proceeding to step (A2) to measure individual samples separately.

EXAMPLE 2

This embodiment provides a mass spectrometry system which differs from Example 1. In this example:

1. No through holes are provided on the bearing member;

2. The guide rail is vertically provided; upper and lower ends of the bearing member are fixed to the support; and the first portions are arranged on the bearing member from the top down. The bearing member is moved up and down so that the individual first portions is located between the ion source and the mass spectrometer.

EXAMPLE 3

This embodiment provides a mass spectrometry system which differs from Example 1. In this example:

A piece of rectangular filter paper is cut out. Several filter paper strips are attached to a side of the rectangular filter paper. Paraffin is printed on the rectangular filter paper, except for some circular are as together with portions connecting the circular areas and the filter paper strips which are not printed with paraffin. The circular are as serve as the first portions, and the areas printed with paraffin serve as the bearing member for supporting the first portions.

EXAMPLE 4

This embodiment illustrate an application of the mass spectrometry system according to Example 3 in the detection of human insulin.

Figure 3:
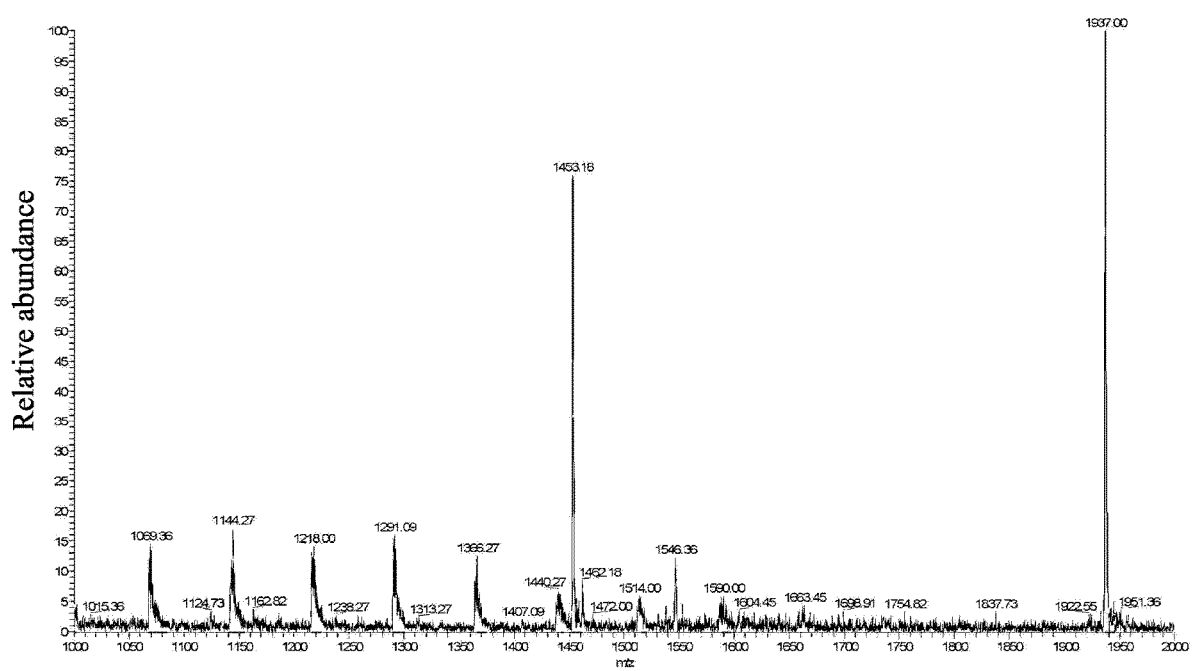
FIG. 3 shows the mass spectrum resulted from the detection of human insulin standard sample.

In this example, a diameter of the first portion is 4 mm; a width and a length of the second portion are 1.5 mm and 8 mm, respectively. The container for containing the sample is a 1 mL centrifuge tube made from polyethylene. The ion source is an open-type ion source. A distance between the nozzle and the sample injection port of the mass spectrometer is 1.5 cm. The sampling device is arranged between the nozzle of the ion source and the sample injection port of the mass spectrometer at a distance of 0.2 mm from the sample injection port of the mass spectrometer. The nozzle of the ion source, the center of the first portion and the sample injection port of the mass spectrometer are in alignment along a horizontal direction. A mass-to-charge ratio (m/z) for mass spectrometry is set at a range from 1,000 to 2,000. A heating temperature of the ion source is set at 100° C., and a flow rate of an inert gas is set at 3 L/min. A human insulin standard at a concentration of 10 ppm (the solvent is a mixed solution of methanol and water at a ratio of 1:1, containing 0.1% acetic acid) is used for analysis, and the mass spectrum result is shown in FIG. 3. Two target signal peaks, 1453.18 (with four charges) and 1937.00 (with three charges) are observed, with intensities of 3.81e2 and 5.01e2, and signal-to-noise ratios of 16.0 and 34.2. The relative standard deviation of the four measurements obtained by moving the motor is 7.23%.

EXAMPLE 5

This embodiment illustrates an application of the mass spectrometry system according to Example 3 in the detection of angiotensin.

Figure 4:
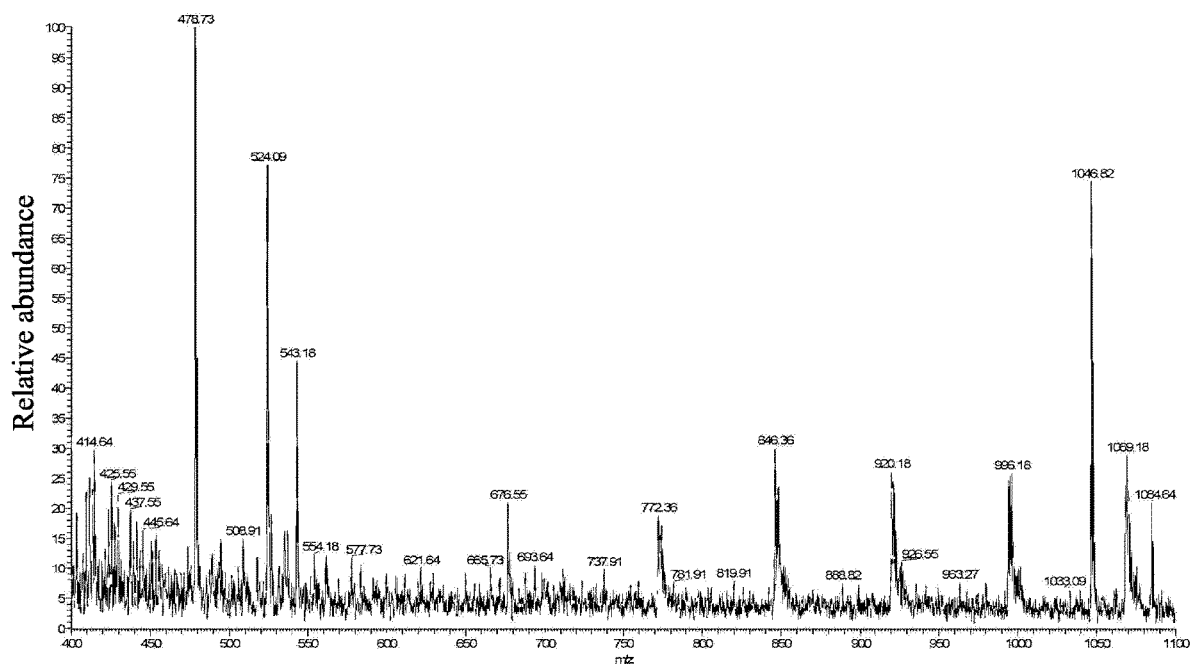
FIG. 4 shows the mass spectrum resulted from the detection of angiotensin standard sample.

In this example, a diameter of the first portion is 3 mm; a width and a length of the second portion are 1.5 mm and 10 mm, respectively. The container for containing the sample is a 1 mL centrifuge tube made from polyethylene. The ion source is an open-type ion source. A distance between the nozzle and the sample injection port of the mass spectrometer is 1.5 cm. The sampling device is arranged between the nozzle of the ion source and the sample injection port of the mass spectrometer at a distance of 0.2 mm from the sample injection port of the mass spectrometer. The nozzle of the ion source, the center of the first portion and the sample injection port of the mass spectrometer are in alignment along a horizontal direction. A mass-to-charge ratio (m/z) for mass spectrometry is set at a range from 400 to 1,100. A heating temperature of the ion source is set at 100° C., and a flow rate of an inert gas is set at 3 L/min. A human insulin standard at a concentration of 10 ppm (the solvent is a mixed solution of methanol and water at a ratio of 1:1, containing 0.1% acetic acid) is used for analysis, and the mass spectrum result is shown in FIG. 4. Two target signal peaks, 524.09 (with two charges) and 1046.82 (with one charges) are observed, with intensities of 2.92e2 and 2.81e2, and signal-to-noise ratios of 5.8 and 12.6. The relative standard deviation of the four measurements obtained by moving the motor is 9.65%.

EXAMPLE 6

This embodiment provides a sampling device for mass spectrometry. The sampling device includes a guide rail, a support, a bearing member, five transport members, five containers corresponding to the five transport members, and a drive module. The guide rail is horizontally provided. The support includes a first support component and a second support component which are arranged vertically. One end of the first support component and one end of the second support component are both connected to the guide rail, and the other end of the first support component and the other end of the second support component are respectively connected to both ends of the bearing member. Thus, the guide rail, the support and the bearing member together form an approximate rectangle. One end of each transport member is connected to the bearing member. The transport members spaced apart are arranged on the bearing member. The other end of each transport member extends into one of the five containers. Each transport member includes a first portion and a second portion. The first portion is arranged on the bearing member. One end of the second portion is connected to the first portion and the other end of the second portion extends into the container. The second portion is arranged vertically. The sampling device further includes a holder for holding the container. Two ends of the holder are connected to a middle of the first support component and a middle of the second support component, respectively.

During the mass spectrum analysis, the drive module drives the support to move on the guide rail such that a central axis of an exit port of the ion source passes through the first portion.

In addition, the mass spectrometry system further includes a position sensor and an alarm device that are connected to each other. Since the support and the transport members thereon containing samples may move, misalignment may occur after the first portion is positioned. With the arrangement of the position sensor and the alarm device, during the mass spectrum analysis, the position sensor can be used to detect whether the nozzle of the ion source is aligned with the center of the first portion. If the nozzle of the ion source is not aligned with the center of the first portion, the alarm device may sound an alarm to indicate the misalignment, such that a more accurate detection result can be obtained.

INDUSTRIAL APPLICABILITY

The mass spectrometry system of the present invention has low background noise in use, and can be used to analyze bio-macromolecular samples enabling an automatic and high-throughput analysis of samples. The sample drop regions can be kept wet for a long time, facilitating the ionization of samples, so as to ensure the sensitivity and reproducibility of analysis. Therefore, the mass spectrometry system of the present invention is suitable for the practical applications.

What is claimed is:

1. A mass spectrometry system, comprising an ion source, a sampling device and a mass spectrometer;
wherein the sampling device comprises:
a guide rail;
a support adapted to move on the guide rail;
a bearing member made from a hydrophobic material; wherein two ends of the bearing member are fixed to the support;
a plurality of containers for containing liquid samples arranged on the support;
a plurality of transport members made from a hydrophilic material; wherein each of the transport members comprises a first portion provided on the bearing member and a second portion connected to the first portion and extending into each of the plurality of containers to be in contact with the sample; the sample contained in each of the containers is delivered to the first portion through the second portion via capillarity to be analyzed; and adjacent transport members are not in contact; and
a drive module configured to drive the support to move on the guide rail such that a central axis of an exit port of the ion source passes through the first portion.

2. The mass spectrometry system according to claim 1, wherein the guide rail and the bearing member are horizontally provided, and the plurality of transport members are vertically provided in a arrangement along a direction parallel to the bearing member.

3. The mass spectrometry system according to claim 1, wherein the guide rail and the bearing member are vertically provided, and first portions of the plurality of transport members are arranged on the bearing member from the top down.

4. The mass spectrometry system according to claim 1, wherein the bearing member and the first portion are different portions of a filter paper; the first portion is a circular portion, and the second portion is a filter paper tape; and one end of the filter paper tape is connected to the first portion and the other end of the filter paper tape extends into the container.

5. The mass spectrometry system according to claim 4, wherein except for an area where the first portion and the second portion overlap with the filter paper, the remainder of the filter paper comprises a hydrophobic material via penetration, and the second portion is free of hydrophobic material.

6. The mass spectrometry system according to claim 5, wherein the hydrophobic material is paraffin.

7. The mass spectrometry system according to claim 1, wherein the first portion has a circular shape with a diameter of 3-5 mm; the second portion has a strip shape with a width of 1-1.5 mm and a length of 5-10 mm.

8. The mass spectrometry system according to claim 1, wherein a distance between a nozzle of the ion source and an injection port of the mass spectrometer is 1.2-1.7 cm; the sampling device is arranged between the ion source and the mass spectrometer; and a distance between the sampling device and the injection port of the mass spectrometer is 0.1-0.3 mm.

9. The mass spectrometry system according to claim 1, wherein the ion source is an open-type ion source.

10. The mass spectrometry system according to claim 1, further comprising:
a position sensor configured to detect alignment of a nozzle of the ion source with a center of the first portion; and and an alarm device configured to sound an alarm when the nozzle is misaligned with the center;

wherein the position sensor is electrically connected to the alarm device.

11. A sampling device for mass spectrometry, comprising:

an ion source;

a guide rail;

a support adapted to move on the guide rail;

a bearing member made from a hydrophobic material; wherein two ends of the bearing member are fixed to the support;

a plurality of containers for containing liquid samples arranged on the support;

a plurality of transport members made from a hydrophilic material; wherein each of the transport members comprises a first portion provided on the bearing member and a second portion connected to the first portion and extending into each of the plurality of containers to be in contact with the sample; the sample contained in each of the containers is delivered to the first portion through the second portion via capillarity to be analyzed; and adjacent transport members being not in contact with each other; and a drive module configured to drive the support to move on the guide rail such that a central axis of an exit port of the ion source passes through the first portion.

* * * * *